United States Patent [19]

Aelony

[11] 4,284,826
[45] Aug. 18, 1981

[54] POLYETHER POLYOLS

[75] Inventor: David Aelony, Beersheva, Israel

[73] Assignee: Makhteshim Chemical Works Ltd., Beersheva, Israel

[21] Appl. No.: 94,879

[22] Filed: Nov. 16, 1979

[30] Foreign Application Priority Data

Nov. 19, 1978 [IL] Israel .................................... 55989

[51] Int. Cl.$^3$ .......................................... C07C 43/13
[52] U.S. Cl. .................... 568/614; 568/676; 521/128
[58] Field of Search ............... 568/614, 676, 681, 844

[56] References Cited

U.S. PATENT DOCUMENTS

| | | | |
|---|---|---|---|
| 3,239,567 | 3/1966 | Kaufman | 568/614 |
| 3,375,207 | 3/1968 | Kaufman | 568/614 X |
| 3,379,778 | 4/1968 | Dowbenko | 568/844 |
| 3,402,169 | 9/1968 | Jackson | 568/614 |
| 3,419,532 | 12/1968 | Jackson | 568/844 |

4,152,497  5/1979  Miano et al. .................. 521/166

*Primary Examiner*—Howard T. Mars
*Attorney, Agent, or Firm*—Browdy and Neimark

[57] ABSTRACT

Low viscosity chlorine containing polyether polyols, and more specifically a low molecular weight, low viscosity diol oligomer of 4,4,4-trichloro-1,2-epoxybutane of the formula

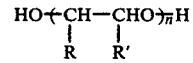

wherein
R and R' are each selected from hydrogen and —CH$_2$CCl$_3$,
wherein R and R' are different, and wherein n is an integer from 2 to 4; is useful in preparing flame retardant polyurethanes.

3 Claims, No Drawings

POLYETHER POLYOLS

FIELD OF THE INVENTION

The present invention pertains to new low viscosity chlorine containing polyether polyols. The present invention is more particularly directed to new low molecular weight, low viscosity diol oligomers of 4,4,4-trichloro-1,2-epoxybutane, to a process for their preparation, to their use as reactive polyols in preparing flame retardant polyurethanes, and to polyurethane compositions containing said novel polyols.

The polyurethanes are an extremely useful group of plastics, having applications in rigid and flexible foams, adhesives, coatings, elastomers, potting resins, in textiles, etc. Polyurethane foams have found wide and varied uses in industry. For example, rigid foams are used as insulators, and semi-rigid and flexible foams are employed in cushioning and packaging applications.

STATE OF THE PRIOR ART

The preparation of polyurethane foams by the reaction of a polyether polyol containing at least two active hydrogen groups, as determined by the Zerwitinoff method, with an organic polyisocyanate in the presence of a foaming agent, a surfactant and a reaction catalyst is well known.

One of the great drawbacks of polyurethane foams, however, is their flammability. Many attempts have been made to impart flame retardance to these materials. These have included incorporating a flame-retardant additive in the polyurethane foam forming reaction mixture, or employing, as polyol reactant in the mixture, certain halogenated polyols. These latter may be prepared by reacting a halogenated alkylene oxide with certain polyhydroxy compounds as is known in the art. For example, U.S. Pat. Nos. 3,402,169 and 3,419,532 disclose polyhalogenous polyhydroxyethers, useful in making non-flammable polymeric products, prepared by reacting a polyhalogenous alkylene oxide, such as trichloropropylene oxide, with a polyhydric alcohol.

In this art of preparing polyhalogenated polyols, 4,4,4-trichloro-1,2-epoxybutane has been recognized to be particularly useful as an intermediate in making polyurethane foam having improved physical properties. Thus, U.S. Pat. Nos. 3,244,754 and 3,269,961 disclose the use of adducts of 4,4,4-trichloro-1,2-epoxybutane and selected polyhydric alcohols in the preparation of flame retardant polyurethane foams.

4,4,4-trichloro-1,2-epoxybutane itself has been subject to hydrolysis to form the 1,2-butane diol. Thus U.S Pat. No. 3,379,778 describes a process for hydrolyzing 4,4,4-trichloro-1,2-epoxybutane with an excess of water by heating it in a water miscible solvent, over a long period of time, and in the presence of a strong aqueous acid, preferably sulfuric acid. The resulting 4,4,4-trichloro-1,2-butanediol is a solid.

Numerous efforts have been made to find the most suitable polyhydric alcohols or mixtures of polyhydric alcohols for reacting with 4,4,4-trichloro-1,2-epoxybutane to give a polyhalogenous polyol commercially practical for preparation of polyurethane foams, particularly rigid foams. For not only must such a polyhalogenous polyol provide the necessary physical properties of the foam, and the required degree of flame retardance, but it must also lend itself to the work techniques in the industry such as ability to be readily handled and formulated.

British Pat. No. 1,092,114, recommends a mixture of pentaerythritol and glycol for preparing an adduct of 4,4,4-trichloro-1,2-epoxybutane. U.S. Pat. No. 3,741,921 recommends dextrose and sucrose based polyols for reacting with 4,4,4-trichloro-1,2-epoxybutane to prepare polyetherpolyols for flame retardant polyurethane foams.

However, these polyether polyols generally have high viscosities which often present serious handling and formulation problems when utilized in the preparation of polyurethane foams. For example, special equipment such as heated feed lines and special stirrers are required. Furthermore, it is known that the use of heat to reduce the viscosity is not a satisfactory solution since the added heat increases the temperature of the resulting polyurethane foam, causing scorching and decomposition thereof. Although liquid blowing agents such as the halogenated hydrocarbons slightly reduce the viscosity of foam systems containing highly viscous polyether polyols the reduction is insufficient to allow the foaming machine to achieve the rapid homogeneity necessary for satisfactory foaming.

In order to overcome this problem, it is suggested in U.S. Pat. No. 3,630,973 to dilute the polyhalogenated polyols with low molecular weight glycols.

SUMMARY OF THE INVENTION

According to the present invention there are provided novel low molecular weight diols of low viscosity which are oligomers of 4,4,4-trichloro-1,2-epoxybutane. Due to the low viscosity, these can be conveniently handled and formulated during the preparation of polyurethane foams. They have a high chlorine content and impart to such foams a satisfactory degree of flame retardance.

The novel oligomers can be blended with conventional less expensive polyols or polyether polyols, and such mixtures still impart the required degree of flame retardance to polymeric foams, and this due to the high chlorine content of the oligomers. This blending permits the custom tailoring of various foams according to given specifications.

The novel polychlorinated polyhydroxy oligomers of the present invention are of the formula

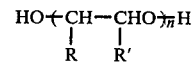

wherein one of R and R' designates hydrogen and the other designates —CH$_2$CCl$_3$, and wherein n is an integer from 2 to 4.

A preferred value of n is 2 to 3.

The new low molecular weight, low viscosity diol oligomers of 4,4,4-trichloro-1,2-epoxybutane of this invention may be prepared by reacting, in a suitable solvent, 4,4,4-trichloro-1,2-epoxybutane with less than an equimolar quantity of water, in the presence of a Lewis acid catalyst. The molar ratio of 4,4,4-trichloro-1,2-epoxybutane to water must be greater than 1 to ensure oligomer formation. This ratio should not exceed 5 in order to prevent formation of higher polymers, such higher polymers being very viscous liquids or even solids. The preferred molar ratio of 4,4,4-trichloro-1,2-epoxybutane to water within the scope of this invention is not more than 3:1 and the most preferred ratio is 2:1 to about 1.1:1. The water reacts with a portion of the 1,2-epoxybutane, under the prescribed reaction conditions, to initially form some 4,4,4-trichloro-1,2-butane diol which instantly undergoes further addition of the 1,2-epoxy butane. The quantity of water, thus controls the molecular weight of the oligomer formed.

The 4,4,4-trichloro-1,2-epoxybutane used in the present invention may be purified and distilled prior to use. Alternatively, the crude 4,4,4-trichloro-1,2-epoxybutane as received from dehydrohalogenation of 2,4,4-tetrachlorobutanol may also be used with no major influence on the course of reaction.

The reaction is carried out in a solvent such as 1,2-dimethoxyethane, dioxane or a low molecular weight ketone, at a preferred temperature of from 60° to 120° C. Similar solvents which are inert to the reaction and which have some water solubility may also be used.

Among the Lewis acids which may be employed as catalysts in the process of the present invention are boron trifluoride, tetrafluoro boric acid, aluminum chloride, antimony pentachloride, titanium chloride, tin tetrachloride, and ferric chloride, with boron trifluoride etherate and tetrafluoro boric acid being referred. A catalytic quantity of these may be used, such as from 0.1 to about 5 parts per 100 parts by weight of the 4,4,4-trichloro-1,2-epoxybutane.

The oligomers of the present invention are light yellow to colorless liquids and have an average molecular weight below 600. Their viscosity is less than 3 stokes and usually it is between 0.5 to 2 stokes. They have great utility in being easily mixed and poured affording homogeneous polyurethane compositions.

Polyurethane foams are prepared by reacting the novel low molecular weight, low viscosity oligomers of 4,4,4-trichloro-1,2-epoxybutane of the present invention, optionally mixed with other polyols, with an organic polyisocyanate in the presence of a foaming agent, a reaction catalyst, and, preferably, a silicone surfactant.

Polyols and polyetherpolyols that can be used in conjunction with the novel low molecular weight, low viscosity oligomers of this invention, are products known in the art as extended polyols or polyether polyols. These may be ethylene oxide or propylene oxide adducts of polyhydroxy compounds such as glycerol, sorbitol, pentaerythritol, other diols and triols and carbohydrate derivatives such as mono- and disaccharides. Epichlorohydrin adducts of polyols may also be blended successfully with the products of this invention.

Any of the widely known organic polyisocyanates can be employed in the preparation of the polyurethane foams of this invention, for example tolylene diisocyanate, which is a mixture of about 80 percent by weight of 2,4-tolylene diisocyanate and 20 percent by weight of the 2,6-isomer. Other typical isocyanates include, but are not limited to the following: methylene-bis-(4-phenyl isocyanate), 3,3'-bitolyene-4,4'-diisocyanate, 3,3'-dimethoxy-4,4'-biphenylene diisocyanate, naphthalene-1,5-diisocyanate, hexamethylene diisocyanate, hexamethylene diisocyanate, 1,4-phenylene diisocyanate, polyphenylene polymethylene isocyanate and the like. The amount of isocyanate employed in the preparation of the polyurethane foams should be sufficient to provide at least about 0.7 NCO group per hydroxyl group present in the reaction system. This includes the number of hydroxyl groups present in the polyol and the surfactant compounds of the present invention, the number of hydroxyl groups in an additives employed, and the number of hydroxyl groups employed in the foaming agent. An excess of isocyanate compound may be conveniently employed; however, this is generally undesirable due to the high cost of the isocyanate compound. It is preferable, therefore, to employ sufficient isocyanate to provide no greater than about 1.5 NCO groups per hydroxyl group, and preferably between about 0.9 and 1.1 NCO groups per hydroxyl group.

The polyurethane foams are prepared in the presence of a foaming agent, reaction catalyst, and preferably a small proportion of a conventional silicone surfactant. The foaming agent employed can be any of those known to be useful for this purpose, such as water, the halogenated hydrocarbons, and mixture thereof. Typical halogenated hydrocarbons include, but are not limited to the following: monofluorotrichloromethane, difluoro dichloromethane, 1,1,2-trichloro-1,2,2-trifluoroethane, methylene chloride, chloroform, and carbon tetrachloride. The amount of foaming agent employed can be varied within a wide range. Generally, however, the halogenated hydrocarbons are employed in an amount from 1 to 50 parts by weight per 100 parts by weight of the polyol and generally water is employed in an amount of from 0.1 to 10 parts by weight per 100 parts by weight of the polyol.

The polyurethane foams are prepared in the presence of a catalytic amount of a reaction catalyst. The catalyst employed can be any of the catalysts known to be useful for this purpose, or mixture thereof, including tertiary amines and metallic salts. Typical tertiary amines include but are not limited to the following: N,N,N',N'-tetramethyl-butanediamine, N-methyl morpholine, N-hydroxyethyl morpholine, triethylene diamine, triethylamine and, trimethylamine. Typical metallic salts include, for example, the salts of antimony, lead, tin and iron, e.g. dibutyltin dilaurate, stannous octoate, and the like. Generally speaking, the catalyst is employed in an amount ranging between about 0.05 and about 1.0, and preferably between about 0.075 and about 0.15 percent by weight, of the polyol.

It is preferred in the preparation of the polyurethane compounds of the present invention to employ minor amounts of a conventional polyurethane foam surfactant in order to further improve the cell structure of the polyurethane foam. Typical of such surfactants are the silicone oils and soaps. Generally up to 2 parts by weight of the surfactant is employed per 100 parts of the polyol. Various additives can be employed which serve to provide different properties, e.g. fillers such as clay, calcium sulfate, or ammonium phosphate may be added to lower cost and improve physical properties. Ingredients such as dyes may be added for color, and fibrous glass, asbestos, cotton ramie or synthetic fibers may be added for strength. In addition, plasticizers, deodorants and antioxidants may be added.

These components are readily reacted in the customary "one-shot" manner to yield a polyurethane foam having excellent physical properties. However, if desired, the "prepolymer" technique, and "quasi" prepolymer technique may also be employed to prepare the novel foams of this invention.

DESCRIPTION OF THE PREFERRED EMBODIMENT

The invention is illustrated with reference to the following illustrative examples, which are to be construed in a non-limitative manner.

EXAMPLE 1

To a solution of 58.5 g (0.33 mole) 4,4,4-trichloro-1,2-epoxybutane in 100 ml 1,2-dimethoxyethane contained in a round bottom flask equipped with a stirrer and condenser was added 6 ml (0.33 mole) water and then 0.3 ml of boron trifluoride etherate. The reaction mixture was heated to 82° C. and refluxed with stirring for a total of four hours. The solvent was removed under vacuum to yield 61.7 g of a light tan liquid residue reflecting the oligomerization of 1.6 moles of 4,4,4-trichloro 1,2-epoxybutane per mole of water. The physical properties of this and all subsequent compounds prepared are listed in Table 1.

EXAMPLE 2

Following the method of Example 1 but using 351 g (2 moles) crude 4,4,4-trichloro-1,2-epoxybutane, 500 ml 1,2-dimethoxyethane, 18 ml (1 mole) water and 1.8 ml boron trifluoride etherate there was obtained after refluxing for six hours and removing the solvent under vacuum 342.4 g of a clear, brown mobile liquid, an oligomer of 1.83 moles of 4,4,4-trichloro-1,2-epoxybutane per mole of water.

EXAMPLE 3

To a solution of 695 g (3.96 mole) crude 4,4,4-trichloro-1,2-epoxybutane in 700 ml recovered 1,2-dimethoxymethane was added 35 ml (1.94 mole) water and the reaction mixture heated to 65° C. Then 1 ml of boron trifluoride etherate was added and the resulting solution refluxed for four and a half and allowed to stand at room temperature overnight. The solvent was removed under vacuum to yield a residue weighing 679.2 g. This reflects the oligomerization of two moles of 4,4,4-trichloro-1,2-epoxybutane per mole of water.

EXAMPLE 4

Following the method of Example 3 but using 702 g (4 mole) purified and distilled 4,4,4-trichloro-1,2-epoxybutane, 700 ml 1,2-epoxybutane, 36 ml (2 mole) water, and 2 ml boron trifluoride etherate there was obtained after refluxing under nitrogen for four hours a liquid residue weighing 703.6 g. This represents 2.24 moles 4,4,4-trichloro-1,2-epoxybutane per mole of water.

EXAMPLE 5

Following the method of Example 3 but using 175.5 g (1 mole) purified and distilled 4,4,4-trichloro-1,2-epoxybutane, 150 ml 1,2-dimethoxyethane, 9 ml (0.5 mole) water, and 0.9 ml boron trifluoride etherate, there was obtained after five and a half hours of reflux a residue weighing 174 g, representing 2.37 moles of 4,4,4-trichloro-1,2-epoxybutane per mole of water.

EXAMPLE 6

Following the method of Example 4 but using 526.5 g (3 mole) purified and distilled 4,4,4-trichloro-1,2-epoxybutane, 500 ml 1,2-dimethoxyethane, 27 ml (1.5 mole) water and 2.5 ml boron trifluoride etherate there was obtained, after refluxing for five hours, a liquid residue weighing 506 g, representing 2.42 moles 4,4,4-trichloro-1,2-epoxybutane per mole of water.

EXAMPLE 7

Following the method of Example 3 but using 1,053 g (6 mole) crude 4,4,4-trichloro-1,2-epoxybutane, 1 liter recovered 1,2-dimethoxyethane, and 54 ml (3 mole) water there was obtained, after refluxing for four hours, a liquid residue weighing 1,072.5 g, representing 2.51 moles 4,4,4-trichloro-1,2-epoxybutane per mole of water.

EXAMPLE 8

Following the method of Example 3 but using 1,404 g (8 moles) purified 4,4,4-trichloro-1,2-epoxybutane, 140 ml 1,2-dimethoxyethane, 72 ml (4 moles) water, and 2 ml boron trifluoride etherate there was obtained after refluxing for four and a half hours, a residue weighing 1,479.4 g, representing 2.54 moles 4,4,4-trichloro-1,2-epoxybutane per mole of water.

EXAMPLE 9

Following the method of Example 4 but using 526.5 g (3 moles) refined 4,4,4-trichloro-1,2-epoxybutane, 500 g 1,2-dimethoxyethane 27 ml (1.5 mole) water, and 2.7 ml boron trifluoride etherate there was obtained a residue weighing 513.3 g, representing 2.65 moles 4,4,4-trichloro-1,2-epoxybutane per mole water.

EXAMPLES 10-19

A series of polyurethane foams were pepared containing a blend of the novel polyhalogenated polyhydroxy oligomer polyols of the present invention, optionally in mixture with other polyols, an organic polyisocyanate, a foaming agent, a reaction catalyst, and a silicone surfactant. The flammability of the resulting foams were evaluated by means of the Oxygen Index Test |ASTM-D2863-70|. Details of the formulations and the results of the flammability tests of these foams are listed in Table 2.

TABLE 1

PHYSICAL PROPERTIES OF OLIGOMERS

| Example | $n_D^t$ | Viscosity (Stokes) | Molecular Weight (Calculated) | OH-Number |
|---|---|---|---|---|
| 1 | $n_D^{22}$ 1.5058 | — | 299.2 | 375 |
| 2 | $n_D^{24.5}$ 1.5000 | — | 340.0 | 330 |
| 3 | $n_D^{24}$ 1.5020 | 1.25 | 366.2 (313; 304)[a] | 304 |
| 4 | $n_D^{21.5}$ 1.5008 | 0.65 | 411 | 273 |
| 5 | $n_D^{27}$ 1.4987 | 0.85–1.0 | 434 | 258.5 |
| 6 | $n_D^{24}$ 1.4995 | 1.0 | 442.6 | 253.5 |
| 7 | $n_D^{25.5}$ 1.4979 | 0.65–0.85 | 458 | 245 |
| 8 | $n_D^{21.5}$ 1.5068 | 1.65–2.0 | 464.6 | 241.5 |
| 9 | $n_D^{27}$ 1.4972 | — | 484.6 | 231.5 |

[a]Experimental

TABLE 2

FORMULATION AND FLAMMABILITY OF POLYURETHANE FOAMS

| EXAMPLE | OLIGOMER FROM EXAMPLE NO. | GRAMS | LS-490[a] (grams) | 5410[b] (grams) | DC-193[b] (grams) | F-11[c] (grams) | H2O (grams) | TMBDA[d] (grams) | UL-2[e] (grams) | MDI[f] (grams) | % Cl[g] IN FOAM | LOI ×10² |
|---|---|---|---|---|---|---|---|---|---|---|---|---|
| 10 | 3 | 60 | 40 | 1.2 | — | 20 | — | 0.2 | 0.2 | 97 | 16.89 | 24 |
| 11 | 3 | 60 | 40 | 1.2 | — | — | 2 | 0.2 | 0.2 | 141 | 13.8 | 23.5 |
| 12 | 3 | 70 | 30 | 1.2 | — | 30 | — | 0.2 | 0.4 | 103 | 19.1 | 25.2 |
| 13 | 3 | 80 | 20 | 1.2 | — | — | 2 | 0.2 | 0.2 | 129 | 19.4 | 26.5 |

TABLE 2-continued

FORMULATION AND FLAMMABILITY OF POLYURETHANE FOAMS

| EXAMPLE | OLIGOMER FROM EXAMPLE NO. | GRAMS | LS-490$^a$ (grams) | 5410$^b$ (grams) | DC-193$^b$ (grams) | F-11$^c$ (grams) | H$_2$O (grams) | TMBDA$^d$ (grams) | UL-2$^e$ (grams) | MDI$^f$ (grams) | % Cl$^g$ IN FOAM | LOI ×10$^2$ |
|---|---|---|---|---|---|---|---|---|---|---|---|---|
| 14 | 3 | 80 | 20 | 1.2 | — | 30 | — | 0.2 | 0.2 | 93 | 23 | 27 |
| 15 | 8 | 70 | 30 | — | 1.2 | 30 | — | 0.2 | 0.4 | 91 | 20.1 | 25.6 |
| 16 | 8 | 80 | 20 | — | 1.2 | - | 2 | 0.2 | 0.2 | 110 | 21.1 | 26.8 |
| 17 | 8 | 70 | 30 | — | 1.0 | 30 | — | 0.2 | 0.2 | 91 | 20.1 | 26.1 |
| 18 | 8 | 80 | 20 | — | 1.0 | — | 2 | 0.2 | 0.2 | 110 | 21.1 | 26.9 |
| 19 | 9 | 60 | 40$^h$ | — | 1.2 | 20 | — | 0.1 | 0.2 | 97 | 16 | 26.5 |

$^a$Sorbitol polyol
$^b$Silicone surfactant
$^c$Freon-11 or equivalent blowing agent
$^d$Tetramethyl Butylene Diamine
$^e$Dibutyltin dilaurate catalyst
$^f$Polymeric crude isocyanate
$^g$Calculated not including the blowing agent
$^h$Atlas-G2410
$^i$Dimethyl cyclohexylamine

We claim:

1. A low molecular weight, low viscosity liquid diol oligomer of 4,4,4-trichloro-1,2-epoxybutane of the formula $$HO\text{+}CH-CHO\text{+}_{\overline{n}}H$$
$$\phantom{HO\text{+}}\;\;\;R\phantom{-}R'$$

wherein
R and R' are selected from hydrogen and —CH$_2$CCl$_3$,
wherein R and R' are different, and wherein n is an integer from 2 to 4.

2. Low molecular weight, low viscosity liquid diol oligomer of 4,4,4-trichloro-1,2-epoxybutane in accordance with claim 1 comprising a mixture of diols.

3. A diol oligomer in accordance with claim 1 having an average molecular weight below 600 and a viscosity of less than 3 stokes.

* * * * *